United States Patent
Mikami et al.

(10) Patent No.: US 6,596,887 B2
(45) Date of Patent: Jul. 22, 2003

(54) PROCESS FOR PRODUCING AN OPTICALLY ACTIVE RUTHENIUM-PHOSPHINE COMPLEX AND PROCESS FOR PRODUCING AN OPTICALLY ACTIVE ALCOHOL BY USING THE COMPLEX

(75) Inventors: Koichi Mikami, Kanagawa (JP); Toshinobu Korenaga, Saitama (JP); Noboru Sayo, Kanagawa (JP)

(73) Assignee: Takasago International Corporation, Tokyo (JP)

(*) Notice: Subject to any disclaimer, the term of this patent is extended or adjusted under 35 U.S.C. 154(b) by 95 days.

(21) Appl. No.: 09/805,364

(22) Filed: Mar. 14, 2001

(65) Prior Publication Data

US 2001/0039354 A1 Nov. 8, 2001

(30) Foreign Application Priority Data

Mar. 14, 2000 (JP) ........................ 2000-070220

(51) Int. Cl.$^7$ ..................... C07F 15/00; B01J 31/00; C07C 29/00
(52) U.S. Cl. ..................... 556/21; 556/23; 556/137; 502/162; 568/814
(58) Field of Search ..................... 556/137, 21, 23; 502/162; 568/814

(56) References Cited

U.S. PATENT DOCUMENTS

| | | | |
|---|---|---|---|
| 5,763,688 A | 6/1998 | Ikariya et al. | 568/814 |
| 6,025,503 A | 2/2000 | Mikami et al. | 549/210 |
| 6,323,353 B1 * | 11/2001 | Sumi et al. | 556/21 |
| 6,372,931 B1 * | 4/2002 | Blacker et al. | 556/136 |
| 6,486,337 B2 * | 11/2002 | Burk et al. | 556/22 |

FOREIGN PATENT DOCUMENTS

EP    0 901 997 A1    3/1999    ......... C07C/29/145

OTHER PUBLICATIONS

Alcock, N., "Substrate–induced Kinetic Resolution of Racemic Biphosphines in situ for Homogeneous Catalysis" J. Chem Soc., Chem, Commun., 1986 p. 1532–1534.
Maruoka, K., "Generation of Chiral Ofganoaluminum Reagent by Discrimination of the Racemates with Chiral Ketone", J.Am. Chem. Soc. 1989, 111, 789–790.
Faller, , J. W., "Chiral Poisoning: A Novel Strategy for Asymmetric Catalysis" J.Am. Chem. Soc. 1993, 804–805.
Ohkuma, T., "Asymmetric Activation of Racemic Ruthenium (II) Complexes for Enantioselective Hydrogenation", J Am. Chem. Soc. 1998, 120, 1086–1087.
Ohkuma, Takeshi et al; "Asymmetric Hydrogenation of Alkenyl, Cyclopropyl, and Aryl Ketones. RuCl2(xylbinap)(1,2–diamine as a Precatalyst Exhibiting a Wide Scope" Journal of the American Chemical Society (1998), 120(51), 13529–13530, 1998 XP002222043.
Doucet, Henri et al; "Trans–'RuCl2(phosphine)2(1,2–diamine)! And chiral trans–'RuCl2(diphosphine)(1–,2–diamine)!:shelf–stable precatalysts for the rapid, productive and steroselective hydrogenation of ketones" Angewandte Chemi, International Edition (1998), 37(12), 1703–1707, 1998 XP002222044.
Mikami, Koich et al: "Conformationally flexible biphenylphosphane ligands for Ru–catalyzed enantioselective hydrogenation" Angewandte Chemi, International Edition (1999), 38(4), 495–497, 1999, XPOO2222045.
Mikami, Koichi et al: "General Synthetic Route to Chiral Flexible Biphenylphosphine Ligands: The Use of a Chiral Additive Enables the Preparation and Observation of Metal Complexes Incorporating the Enantiopure Form" Organic Letters (2001), 3(2), 243–245, 2001, XP002222046.
Mikami, Koichi et al: "Asymmetric activation/deactivation of racemic Ru catalysts for highly enantioselective hydrogenation of ketonic substrates" Angewandte Chemie, International Edition (2000), 39(20), 3707–3710, 2000 XP002222047.
Ohkuma, T. et al: "Asymmetric activation of racemic ruthenium (II) complexes for enantioselective hydrogenation" Journal of the American Chemical Society, vol. 120, 1998, pp. 1086–1087, XP002222048.

* cited by examiner

Primary Examiner—Porfirio Nazario-Gonzalez
(74) Attorney, Agent, or Firm—Sughrue Mion, PLLC

(57) ABSTRACT

Provided is a process for preparing an optically active ruthenium-phosphine complex represented by the following formula (1):

(1)

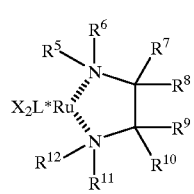

wherein L represents a bidentate ligand compound of a tertiary phosphine; X represents a halogen atom; and * means chiral center (L* is an optically active substance), which comprises reacting a ruthenium-phosphine complex represented by:

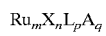

or

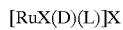

wherein, X and L have the same meanings as described above (L is a racemic modification); A represents triethylamine ($Et_3N$), etc.; and m, n, p and q each stands for an integer and D represents benzene, etc. with ½ equivalent of a specific optically active chiral diamine, thereby inactivating one of the enantiomers; and then with a specific optically active diamine derivative, thereby activating the other enantiomer.

1 Claim, No Drawings

PROCESS FOR PRODUCING AN OPTICALLY ACTIVE RUTHENIUM-PHOSPHINE COMPLEX AND PROCESS FOR PRODUCING AN OPTICALLY ACTIVE ALCOHOL BY USING THE COMPLEX

FIELD OF THE INVENTION

1. Field of the Invention

The present invention relates to a process of reacting a racemic ruthenium phosphine complex with ½ equivalent of an optically active diamine having chiral asymmetric activity, thereby inactivating one of the enantiomers, adding an optically active diamine derivative to the other portion of the optically active ruthenium-phosphine complex and thus preparing a ruthenium complex having an optically active diphosphine and an optically active diamine derivative coordinated therein; and a process for preparing an optically active alcohol by making use of the complex.

2. Description of the Related Art

It is known that a complex formed of a transition metal atom and an organic ligand is used as an asymmetric reaction catalyst. It is also known that an optically active compound, particularly an axially asymmetric diphosphine ligand compound, is selected as the organic ligand. The axially asymmetric diphosphine ligand compound tends to be very expensive and is therefore disadvantageous for industrial use.

Use of a racemic catalyst, if possible, will be advantageous for the preparation of an inexpensive optically active compound. Two methods are reported for asymmetric synthesis in the presence of a racemic catalyst, that is, (1) a method making use of an asymmetric inactivating agent and (2) a method making use of an asymmetric activating agent.

(1) In "asymmetric inactivating method" which is also called as "chiral poisoning", one of the enantiomers of a racemic catalyst is subjected to selective complex formation/inactivation and reaction is conducted in the presence of the other enantiomer catalyst. For asymmetric inactivation, enantioselective complex formation is an absolute requirement.

Several reports have so far been made on asymmetric synthesis by using an asymmetric ligand or a metal complex in the racemic form. For example, there is a report in J. M. Brown, et al., *J. Chem. Soc., Chem. Commun.*, 1532(1986) that an optically pure iridium complex in the (S)-form is allowed to act on CHIRAPHOS (2,3-bisdiphenyl-phosphinobutane) in the racemic form to form a complex with CHIRAPHOS in the (R)-form and then, the remaining CHIRAPHOS in the (S)-form is made use of as a rhodium complex for asymmetric hydrogenation reaction of dehydroamino acid. It is also reported that a chiral ketone is added to a racemic binaphthol-aluminum complex to inactivate the binaphthol-aluminum complex in the (R)-form by forming a complex therewith and then the remaining binaphthol-aluminium complex in the (S)-form takes part in asymmetric Diels-Alder reaction (H. Yamamoto et al., *J. Am. Chem. Soc.*, 111, 789(1989)), or that a methionine-derived phosphine ligand is added as an inactivating agent to a racemic rhodium complex to inactivate one of the enantiomers thereof, whereby asymmetric hydrogenation of dehydroamino acid is conducted (J. W. Faller et al., *J. Am. Chem. Soc.*, 115, 804(1993)).

In the above-described three examples, an enantioselectivity is not so high, suggesting that an inactivated enantiomer complex is not selectively formed.

(2) "Asymmetric activation" of a racemic catalyst means that an asymmetric activating agent forms a complex selectively with one of the enantiomers of the racemic catalyst, thereby imparting it with higher catalytic activity than that of the catalyst before reaction and in the presence of this catalyst imparted with a higher catalytic activity, catalytic asymmetric synthesis is conducted. Even if an enantioselective complex cannot be formed, there is a diastereiomer relationship between two complexes thus formed, for example, (S)-catalyst/(S)-activating agent and (R)-catalyst/(S)-activating agent so that they must be different each other in catalytic activity. If the difference is large, a high enantioselectivity can be attained. Mikami, who is one of the present inventors, and et al., reported catalytic asymmetric hydrogenation which is effected by asymmetric activation and can permit attainment of a high enantio-selectivity even in the presence of a racemic BINAP (2,2'-bis(diphenylphosphino)-1,1'-binaphthyl)-Ru catalyst (T. Ohkuma et al., *J. Am. Chem Soc.*, 120, 1086(1998)). In this hydrogenation reaction, the asymmetric activating agent forms a complex with each of the enantiomers of the racemic catalyst, thereby forming two activated diastereomer complexes. These two activated complexes in a diastereomeric relation differ largely in catalytic activity and a high enantio-selectivity can be attained, which however depends on the ketone substrate. This method is however accompanied with the problems that a high enantio-selectivity cannot be attained without a large difference between two activated complexes in catalytic activity; and the difference between two activated complexes in catalytic activity depends largely on the ketone substrate to be employed, meaning that the ketone substrate is not generally used.

SUMMARY OF THE INVENTION

The present inventors considered that a more efficient racemic catalyst reaction system can be provided by using two methods for a racemic catalyst, that is, asymmetric activation and asymmetric inactivation in combination and making synergistic use of their merits rather than by using them independently. Described specifically, they considered that if it is possible to inactivate only one of the enantiomers of a racemic catalyst, thereby obtaining only an activated diastereomer complex composed of the other enantiomer, the asymmetric activating method of a racemic BINAP-Ru catalyst improves an enantio-selectivity further and enlarge the application range of its ketone substrate.

With a view toward overcoming the above-described problems, the present inventors have carried out an extensive investigation. As a result, it has been found that an enantio-selectivity as high as that obtained by asymmetric activation of an optically pure catalyst can be attained by an optically active ruthenium-phosphine complex obtained by subjecting one of the enantiomers of a racemic BINAP-Ru complex to complexation and inactivation by using an inactivating agent and then, adding an asymmetric activating agent to form a complex with the other enantiomer; and that in the presence of the above-described complex, hydrogenation reaction of a carbonyl compound proceeds whereby an optically active alcohol is available at a high optical purity and high yield, leading to the completion of the invention.

The following are the aspects of the invention.

1) A process for producing an optically active ruthenium-phosphine complex represented by the following formula (1):

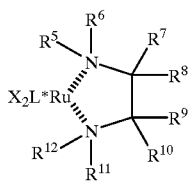

(1)

wherein $R^5$, $R^6$, $R^{11}$ and $R^{12}$ each independently represents a hydrogen atom, a saturated or unsaturated hydrocarbon group, an aryl group, a urethane group or a sulfonyl group; $R^7$, $R^8$, $R^9$ and $R^{10}$ are the same or different so that the carbon to which these substituents have been bonded become an asymmetric center and each independently represents a hydrogen atom, an alkyl group, an aromatic monocyclic or polycyclic group, a saturated or unsaturated hydrocarbon group or a cyclic hydrocarbon group; or $R^7$ or $R^8$ and $R^9$ or $R^{10}$ may be coupled together to form an alicyclic group so that the carbon bonded thereto becomes an asymmetric center; L represents a bidentate ligand compound of a tertiary phosphine; X represents a halogen atom; and * means chiral center (L* is an optically active substance), which comprises reacting a ruthenium-phosphine complex represented by the following formula (2):

$$Ru_mX_nL_pA_q \qquad (2)$$

wherein X and L have the same meanings as described above (L is a racemic modification); A represents triethylamine ($Et_3N$) or dimethylformamide (DMF); and m, n, p and q each stands for an integer and when A represents $Et_3N$, m, n, p and q stand for 2, 4, 2 and 1, respectively, and when A represents DMF, m, n, p and q stand for 1, 2, 1 and 2 to 5, respectively; or a ruthenium phosphine complex represented by the following formula (3):

$$[RuX(D)(L)]X \qquad (3)$$

wherein, X and L have the same meanings as described above (L is a racemic modification), and D represents benzene, p-cymene, 1,3,5-trimethylbenzene or hexamethylbenzene, with the ½ equivalent of an optically active chiral diamine represented by the following formula (4):

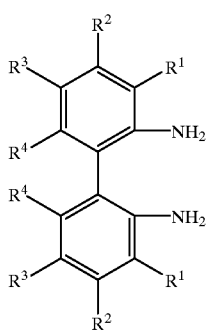

(4)

wherein $R^1$ represents a $C_{1-4}$ lower alkyl group, $R^2$ represents a hydrogen atom, a methyl group or a methoxy group, $R^3$ represents a hydrogen atom, a methyl group, a methoxy group or a chlorine atom, $R^4$ represents a methyl group, a methoxy group or a trifluoromethyl group, or $R^3$ and $R^4$ may be coupled together to form a cyclo ring, thereby inactivating only one of the enantiomers, and then reacting the resulting compound with an optically active diamine derivative represented by the following formula (5):

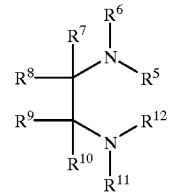

(5)

wherein, $R^5$, $R^6$, $R^7$, $R^8$, $R^9$, $R^{10}$, $R^{11}$ and $R^{12}$ have the same meanings as defined above, thereby activating the other enantiomer 2) A process for producing an optically active alcohol represented by the following formula (7):

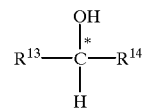

(7)

wherein * means chiral center, $R^{13}$ represents a substituted or unsubstituted monocylic or polycyclic aromatic hydrocarbon group or an α,β-unsaturated $C_{2-10}$ alkyl group and $R^{14}$ represents a substituted or unsubstituted, saturated or unsaturated $C_{1-10}$ hydrocarbon group or a substituted or unsubstituted monocyclic or polycyclic aromatic hydrocarbon group, or $R^{13}$ and $R^{14}$ may be coupled together to form a saturated or unsaturated alicyclic group which may have a substituent for providing a cyclic ketone, which comprises subjecting, in the presence of an optically active ruthenium-phosphine complex as described above in 1) as a catalyst and a base, a ketone compound represented by the following formula (6):

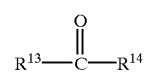

(6)

wherein $R^{13}$ and $R^{14}$ have the same meanings as described above, to asymmetric hydrogenation.

3) A process for producing an optically active alcohol compound as described above in 2), wherein the base is an alkali metal compound or an alkali earth metal compound.

4) A binaphthyldiamine derivative represented by the following formula (4'):

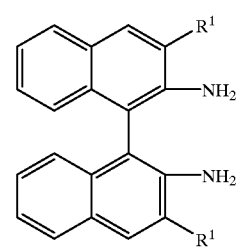

(4')

wherein $R^1$ represents a $C_{1-4}$ lower alkyl group.

DETAILED DESCRIPTION OF THE INVENTION

The invention will next be described more specifically.

As a ruthenium-phosphine complex to be used in the invention, a ruthenium-phosphine complex represented by the following formula (2):

$$Ru_mX_nL_pA_q \tag{2}$$

wherein X represents a halogen atom; L represents a bidentate ligand compound of a tertiary phosphine (L is a racemic modification); A represents triethylamine ($Et_3N$) or dimethylformamide (DMF); and m, n, p and q each stands for an integer and when A represents $Et_3N$, m, n, p and q stand for 2, 4, 2 and 1, respectively, and when A represents DMF, m, n, p and q stand for 1, 2, 1 and 2 to 5, respectively; or a ruthenium phosphine complex represented by the following formula (3):

$$[RuX(D)(L)]X \tag{3}$$

wherein X represents a halogen atom, L represents a bidentate ligand compound of a tertiary phosphine (L is a racemic modification); and D represents benzene, p-cymene, 1,3,5-trimethylbenzene or hexamethylbenzene.

Specific examples of the L which is a tertiary phosphine include phosphine compounds represented by the following formula (8):

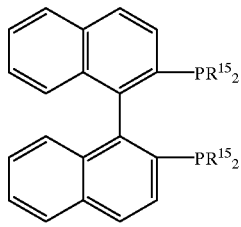

(8)

wherein, $R^{15}$ represents a phenyl, 4-methylphenyl, 3-methylphenyl, 3,5-dimethylphenyl, 4-methoxyphenyl, cyclohexyl or cyclopentyl group (JP-A-3-20290 (the term "JP-A" as used herein means an "unexamined published Japanese patent application), JP-3-255090, JP-4-74192). Examples of the tertiary phosphine include, in addition to those of the formula (8), those represented by the formula (9):

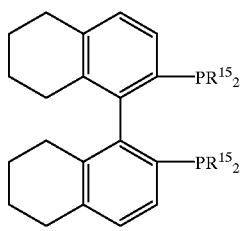

(9)

wherein $R^{15}$ represents a phenyl, 4-methylphenyl, 3-methylphenyl, 3,5-dimethylphenyl, 4-methoxyphenyl, cyclohexyl or cyclopentyl group (JP-4-139140). Examples of the tertiary phosphine include, in addition to the above-exemplified ones, those represented by the formula (10):

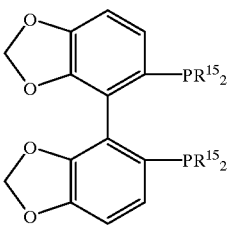

(10)

wherein $R^{15}$ represents a phenyl, 4-methylphenyl, 3-methylphenyl, 3,5-dimethylphenyl, 4-methoxyphenyl, cyclohexyl or cyclopentyl group (JP-10-182678). Examples of the tertiary phosphine include, in addition to the above-exemplified ones, those represented by the formula (11):

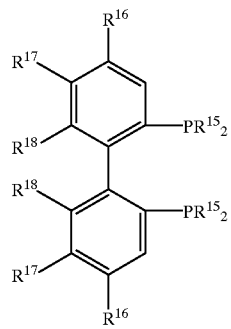

(11)

wherein $R^{15}$ represents a phenyl, 4-methylphenyl, 3-methylphenyl, 3,5-dimethylphenyl, 4-methoxyphenyl, cyclohexyl or cyclopentyl group, $R^{16}$ represents a hydrogen atom, a methyl group or a methoxy group, $R^{17}$ represents a hydrogen atom, a methyl group, a methoxy group or a chlorine atom, and $R^{18}$ represents a methyl, methoxy or trifluoromethyl group. Examples of the optically active tertiary phosphine include (4,4',6,6'-tetramethyl-5,5'-dimethoxybiphenyl-2,2'-diyl)-bis(diphenylphosphine) and, ((4,4',6,6'-tetramethyl-5,5'-dimethoxybiphenyl-2,2'-diyl)-bis(di-p-methoxyphenylphosphine) as described in *Chem. Pharm. Bull.*, 39, 1085(1991); (4,4',6,6'-tetratrifluoromethylbiphenyl-2,2'-diyl)-bis(diphenylphosphine) and (4,6-ditrifluoromethyl-4',6'-dimethyl-5'-methoxybiphenyl-2,2'-diyl)-bis(diphenylphosphine) described in *Synlett*, 827 (1991); and 2-dicyclohexyl-2'-diphenylphosphino-4,4',6,6'-tetramethyl-5,5'-dimethoxybiphenyl-2,2'-diyl)-bis(diphenylphosphine) described in *Tetrahedron: Asymmetry*, 3, 13(1992).

Optically active tertiary phosphines disclosed in JP-B-4-115796 (the term "JP-B" as used herein means an "examined Japanese patent publication") are also usable. Examples include (6,6'-dimethyl-2,2'-biphenylene)-bis(diphenylphosphine), (4,4',6,6'-tetramethyl-2,2'-biphenylene)-bis(diphenylphosphine), (3,3',6,6'-tetramethyl-2,2'-biphenylene)-bis(diphenylphosphine), (4,4'-difluoro-6,6'-dimethyl-2,2'-biphenylene)-bis(diphenylphosphine), (4,4'-bis(dimethylamino)-6,6'-dimethyl-2,2'-biphenylene)-bis(diphenylphosphine), (6,6'-dimethyl-2,2'-biphenylene)-bis(di-p-tolylphosphine), (6,6'-dimethyl-2,2'-biphenylene)-bis(di-o-tolylphophine), (6,6'-dimethyl-2,2'-biphenylene)-bis(di-m-fluorophenylphosphine), and 1,11-bis(diphenylphosphino)-5,7-dihydrodibenzo[c,e]oxepine. Also usable are those disclosed in JP-A-3-5492 such as (6,6'-dimethoxybiphenyl-2,2'-diyl)-bis(diphenylphosphine), (5,5',6,6'-tetramethoxybiphenyl-2,2'-diyl)-bis(diphenylphosphine), (6,6'-dimethoxybiphenyl-2,2'-diyl)-bis(di-p-tolylphosphine) and (4,4',5,5',6,6'-tetrahexamethoxybiphenyl-2,2'-diyl)-bis(diphenylphosphine).

Examples of the phosphine compound include, in addition to the above-exemplified ones, those represented by the following formula (12):

(12)

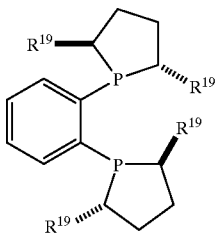

wherein $R^{19}$ represents a methyl, ethyl, propyl or isopropyl group. Examples of the optically active tertiary phosphine include 1,2-bis(2,5-dimethylphosphorano)benzene, 1,2-bis(2,5-diethylphosphorano)benzene, 1,2-bis(2,5-dipropylphosphorano)benzene and 1,2-bis(2,5-diisopropylphosphorano)benzene as described in *J. Am. Chem. Soc.*, 115, 10125(1993).

Examples of the phosphine compound include, in addition to the above-exemplified ones, CHIPAPHOS (2,3-bis-(diphenylphosphino)butane (13), PROPHOS (1,2-bis-(diphenylphosphino)propane) (14), NORPHOS (5,6-bis-(diphenylphosphino)-2-norbornene) (15), DEGPHOS (1-substituted-3,4-bis-(diphenylphosphino)pyrrolidine) (16), BDPP (2,4-bis(diphenylphosphino)pentane) (17), DIOP (2,3-o-isopropylidene-2,3-dihydroxy-1,4-bis-(diphenylphosphino)butane) (18), DIPAMP (1,2-bis-[(o-methoxyphenyl)phosphino]ethane) (19), BPPHFOH (1-[1'-bis-(diphenylphosphino)ferrocenyl]ethanol) (20), and BPPM (1-tert-butoxycarbonyl-4-diphenylphosphino-2-diphenylphosphinomethylpyrrolidine (21).

13

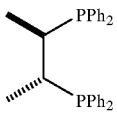

14

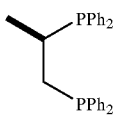

15

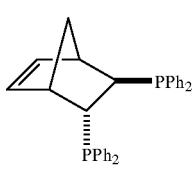

16

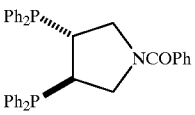

17

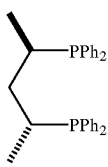

18

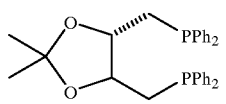

19

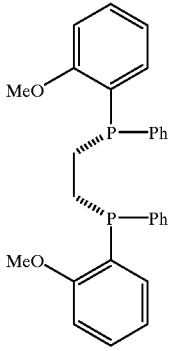

20

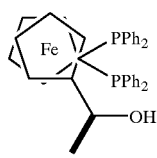

21

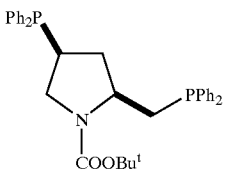

In the invention, an optically active diamine compound is used as an optically inactivating agent. Examples include optically active chiral diamine compounds each represented by the following formula (4):

(4)

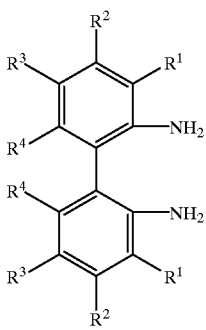

wherein $R^1$ represents a $C_{1-4}$ lower alkyl group, $R^2$ represents a hydrogen atom, a methyl group or a methoxy group, $R^3$ represents a hydrogen atom, a methyl group, a methoxy group or a chlorine atom, $R^4$ represents a methyl group, a methoxy group or a trifluoromethyl group, or $R^3$ and $R^4$ may be coupled together to form a cyclo ring.

Specific examples include optically active 3,3'-dimethyl-2,2'-diamino-1,1'-binaphthyl of the following formula (22):

(22)

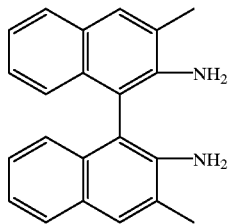

optically active 3,3'-dimethyl-2,2'-diamino-5,5',6,6',7,7',8,8'-octahydro-1,1'-binaphthyl of the following formula (23):

(23)

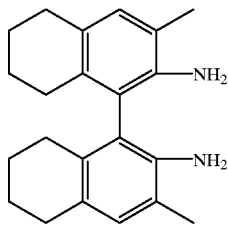

and optically active 3,3',4,4',6,6'-hexamethyl-2,2'-diamino-1,1'-biphenyl of the following formula (24):

(24)

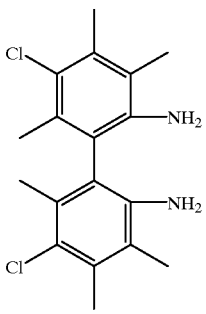

In the invention, an optically active amine compound or the like is employed as an optically activating agent. Examples include optically active diamine compounds each represented by the following formula (5):

(5)

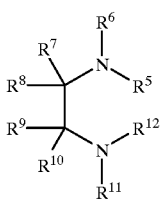

wherein $R^5$, $R^6$, $R^{11}$ and $R^{12}$ each independently represents a hydrogen atom, a saturated or unsaturated hydrocarbon group, an aryl group, a urethane group, a sulfonyl group or the like; $R^7$, $R^8$, $R^9$ and $R^{10}$ are the same or different so that the carbon to which these substituents are bonded becomes an asymmetric center and each represents a hydrogen atom, an alkyl group, an aromatic monocyclic or polycyclic group, a saturated or unsaturated hydrocarbon group or a cyclic hydrocarbon group; or $R^7$ or $R^8$ and $R^9$ or $R^{10}$ may be coupled together to form an alicyclic group so that the carbon bonded thereto becomes an asymmetric center.

Specific examples include optically active diamine compounds such as optically active 1,2-diphenylethylenediamine, 1,2-cyclohexanediamine, 1,2-cycloheptanediamine, 2,3-dimethylbutanediamine, 1-methyl-2,2-diphenylethylenediamine 1-isobutyl-2,2-diphenylethylenediamine, 1-isopropyl-2,2-diphenylethylenediamine, 1-methyl-2,2-di(p-methoxyphenyl)ethylenediamine, 1-isopropyl-2,2-di(p-methoxyphenyl)ethylenediamine, 1-isopropyl-2,2-di(p-methoxyphenyl)ethylenediamine, 1-benzyl-2,2-di(p-methoxyphenyl)ethylenediamine, 1-methyl-2,9-dinaphthylethylenediamine, 1-isobutyl-2,2-dinaphthylethylenediamine and 1-isopropyl-2,2-dinaphthylethylenediamine and optically active diamine compounds having a sulfonyl or urethane group as one or two of the substituents of $R^5$ to $R^{12}$. The diamine compound is used in an amount of 0.5 to 2.5 equivalents, preferably 1 to 2 equivalents relative to the transition metal complex.

As an organic solvent to be used upon preparation of the complex of the invention, no particular limitation is imposed insofar as it does not react with the ruthenium-phosphine complex easily. Preferred examples include aromatic hydrocarbons such as benzene, toluene and xylene, halogenated hydrocarbons such as methylene chloride, chloroform and carbon tetrachloride and aprotic solvents such as tetrahydrofuran, diethyl ether and dimethoxyethane. The reaction temperature can be set within a range of from 0° C. to 30° C. The reaction time varies, depending on the kind of the organic solvent, ruthenium-phosphine complex, inactivating agent (optically active chiral diamine (4)) or activating agent (optically active diamine derivative (5)) to be employed, but is usually set within a range of from 10 to 180 minutes, preferably 30 to 60 minutes.

The present invention also provides a process for producing an optically active alcohol represented by the following formula (7):

(7)

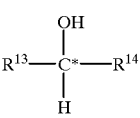

wherein * means chiral center, $R^{13}$ represents a substituted or unsubstituted, monocylic or polycyclic aromatic hydrocarbon group or an $\alpha,\beta$-unsaturated $C_{2-10}$ alkyl group and $R^{14}$ represents a substituted or unsubstituted, saturated or unsaturated $C_{1-10}$ hydrocarbon group or a substituted or unsubstituted monocyclic or polycyclic aromatic hydrocarbon group, or $R^{13}$ and $R^{14}$ may be coupled together to form a saturated or unsaturated alicyclic group which may have a substituent for providing a cyclic ketone, which comprises subjecting, in the presence of an optically active ruthenium-phosphine complex as described above as a catalyst and a base, a ketone compound represented by the following formula (6):

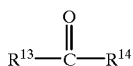

(6)

wherein $R^{13}$ and $R^{14}$ have the same meanings as described above, to asymmetric hydrogenation.

Examples of the substituted or unsubstituted hydrocarbon group or heterocylic group represented by $R^{13}$ or $R^{14}$ of the carbonyl compound of the formula (6) employed as a raw material in the process of the invention include substituted or unsubstituted aliphatic hydrocarbon groups, monocylic or polycyclic aromatic hydrocarbon groups, monocyclic or polycyclic alicyclic hydrocarbon groups, and monocyclic or polycyclic heterocylic groups. Among them, as the aliphatic hydrocarbon groups, saturated or unsaturated, linear or branched hydrocarbon groups can be given as examples. Specific examples include alkyl groups such as methyl, ethyl, propyl, butyl, pentyl, hexyl and heptyl and alkenyl groups such as vinyl and allyl. Specific examples of the monocyclic or polycyclic aromatic hydrocarbon group include phenyl, 2-methylphenyl, 2-ethylphenyl, 2-isopropylphenyl, 2-tert-butylphenyl, 2-methoxyphenyl, 2-chlorophenyl, 2-vinylphenyl, 3-methylphenyl, 3-ethylphenyl, 3-isopropylphenyl, 3-methoxyphenyl, 3-chlorophenyl, 3-vinylphenyl, 4-methylphenyl, 4-ethylphenyl, 4-isopropylphenyl, 4-tert-butylphenyl, 4-vinylphenyl, cumenyl, mesityl, xylyl, 1-naphthyl, 2-naphthyl, anthryl, phenanthryl and indenyl. Specific examples of the monocyclic or polycyclic alicyclic hydrocarbon group include cycloalkyl groups such as cyclopropyl, cyclobutyl, cyclopentyl and cyclohexyl. Specific examples of the monocyclic or polycyclic heterocyclic group include thienyl, furyl, pyranyl, xanthenyl, pyridyl, imidazolinyl, indolyl, carbazoyl and phenanthrolyl. Examples of the substituent for these groups include halogen atoms, hydroxyl group and alkoxyl groups. Also aralkyl groups or ferrocenyl group can be given as the substituent when the above-exemplified hydrocarbon group and heterocyclic group are bonded each other.

Examples of the aliphatic ring formed by $R^{13}$ and $R^{14}$ together with an adjacent carbon atom include 5 to 12-membered cyclic ketones such as cyclopentanone, cyclohexanone, cycloheptanone, cyclohexenone and cycloheptenone. These cyclic ketones may be substituted with an alkyl, alkenyl, aromatic hydrocarbon, heterocyclic or alkoxyl group.

As $R^{13}$, particularly preferred are aliphatic hydrocarbon groups, aromatic hydrocarbon groups and heterocyclic groups, while as $R^{14}$, aliphatic hydrocarbon groups are preferred, with alkyl groups being particularly preferred. It is also preferred that $R^{13}$ and $R^{14}$ are coupled together with an adjacent carbon atom to form a substituted or unsubstituted cyclic ketone.

As the base, metal salts each represented by the following formula (25):

MZ   (25)

wherein M represents an alkali metal or alkaline earth metal and Z represents a hydroxy, alkoxy, mercapto, naphthyl group or carbonate, or quaternary ammonium salts can be employed. Specific examples include LiOH, LiOMe, LiOEt, LiOCH(CH$_3$)$_2$, LiOC(CH$_3$)$_3$, NaOH, NaOMe, NaOEt, NaOCH(CH$_3$)$_2$, NaOC(CH$_3$)$_3$, KOH, KOMe, KOEt, KOCH(CH$_3$)$_2$, KOC(CH$_3$)$_3$, KC$_{10}$H$_8$, K$_2$CO$_3$ and Na$_2$CO$_3$. Quaternary ammonium salts are also usable. The base is used in an amount of 0.5 to 100 equivalents, preferably 2 to 4 equivalents relative to the transition metal complex.

In the invention, two catalyst components, that is, the optically active ruthenium-phosphine complex of the formula (1) and base, are indispensable for smooth progress of asymmetric hydrogenation reaction and attainment of a high optical yield. An alcohol having a high reaction activity and high optical purity is not available without both components. In the invention, any liquid solvent is usable insofar as it can solubilize reaction raw materials and catalyst system. Examples include aromatic hydrocarbon solvents such as toluene and xylene, aliphatic hydrocarbon solvents such as pentane and hexane, halogen-containing hydrocarbon solvents such as methylene chloride, ether solvents such as ether and tetrahydrofuran, alcohol solvents such as methanol, ethanol, 2-propanol, butanol and benzyl alcohol, and hetero-atom-containing organic solvents such as acetonitrile, DMF and DMSO. The target product is an alcohol so that alcohol solvents are most suited, with 2-propanol being more preferred. When the reaction substrate cannot be solubilized in a solvent easily, a mixture of the solvents selected from the above-exemplified ones can be employed.

The amount of the solvent is judged from the solubility of the reaction substrate and economy. When 2-propanol is employed, reaction can be effected at a low concentration of 1% or less or in a nearly solventless manner, though depending on the kind of the substrate. Preferred is 20 to 50 % by weight. The hydrogen pressure in the invention is preferably 1 atmospheric pressure because this catalyst system has markedly high activity. In consideration of the economy, however, the hydrogen pressure within a range of 1 to 100 atmospheric pressure is desired, with 3 to 50 atmospheric pressure being more preferred. It is possible to maintain high activity even at a pressure of 10 atmospheric pressure or less when economy of the whole process is taken into consideration.

Although the reaction is preferably conducted at a temperature within 0 to 140° C., it can be conducted within a range of 30 to 100° C. The reaction time differs with the concentration of the reaction substrate or reaction conditions such as temperature and pressure, but reaction is completed within several minutes to 10 hours. The reaction of the invention can be conducted batchwise or continuously.

The invention further provides a novel binaphthyldiamine derivative represented by the following formula (4'):

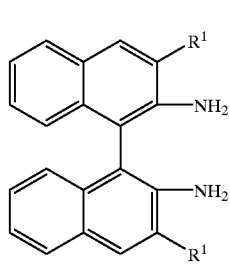

(4')

wherein $R^1$ represents a $C_{1-4}$ lower alkyl group.

In this binaphthyldiamine derivative (4'), specific examples of the $C_{1-4}$ lower alkyl group as $R^1$ include methyl, ethyl, propyl, isopropyl, butyl, isobutyl, sec-butyl and tert-butyl groups.

The compound (4') of the invention can be prepared in accordance with the below-described reaction scheme. In this reaction scheme (4'), a binaphthyldiamine derivative having as $R^1$ a methyl group is prepared.

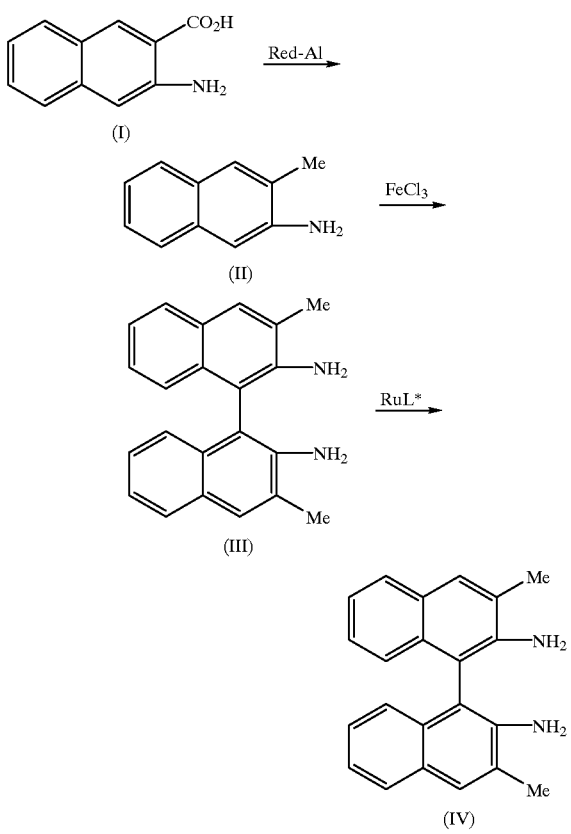

Optically active 3,3'-dimethyl-1,1'-binaphthyl-2,2'-diamine (IV) is available by reducing 2-aminonaphthoeic acid (I), which is used as a raw material, with "Red-Al" (trade name, a toluene solution of bis(2-methoxyethoxy) aluminum sodium hydride) to obtain 3-metyl-2-naphthylamine (II), subjecting it to dimerization by using $FeCl_3$ to obtain 3,3'-dimethyl-1,1'-binaphthyl-2,2'-diamine (III) and then subjecting it to optical resolution by using optically active RuL* (optically active ruthenium-phosphine complex, for example, $RuCl_2[binap](dmf)_n$).

The above-described reaction can also be applied to the compound (4') other than that having as $R^1$ a methyl group.

The invention compound (4') thus available is useful for inactivating one of the enantiomers of the racemic ruthenium-phosphine complex.

EXAMPLES

The present invention will hereinafter be described in detail by Examples. It should however be borne in mind that the present invention is not limited to or by them.

Apparatuses employed for measurement of each substance are as follows:

$^1H$ Nuclear magnetic resonance spectrum (which will hereinafter be abbreviated as "$^1H$-NMR"):
  "GEMINI-300" (300 MHz) (trade name; product of Varian, Inc.)
$^{13}C$ Nuclear magnetic resonance spectrum (which will hereinafter be abbreviated as "$^{13}C$-NMR"):
  "GEMINI-300" (75 MHz) (trade name; product of Varian, Inc.)
Polarimeter: "DIP-140" (trade name; product of JASCO Corporation)

High-performance liquid chromatography (which will hereinafter be abbreviated as "HPLC")
  "LC-6A", "SPD-6A" (trade name; product of Shimadzu Corporation)
Gas chromatography (which will hereinafter be abbreviated as "GC")
  "Shimadzu GC-14B" (trade name; product of Shimadzu Corporation)

Abbreviations employed in this specification have the following meanings.

(±): racemic form
binap: 2,2'-bis(diphenylphosphino)-1,1'-binaphthyl
dm-binap: 2,2'-bis[di(3,5-dimethylphenyl)phosphino]-1,1'-binaphthyl
dmf: dimethylformamide
dpen: 1,2-diphenylethylenediamine

Example 1

Synthesis of 3,3'-dimethyl-1,1'-binaphthyl-2,2'-diamine
1) Synthesis of 3-methyl-2-naphthylamine Under an argon gas stream, 12.1 g (52 mmol) of 2-aminonaphthoeic acid (80% purity) was dissolved in 350 mL of xylene, followed by the dropwise addition of 117 mL (390 mmol) of Red-Al (trade name; a toluene solution of sodium bis(2-methoxyethoxy)aluminum hydride). After stirring at 150° C. for 6 hours, the reaction mixture was cooled and 39 mL (130 mmol) of Red-Al was added dropwise further. After stirring at 150° C. for 18 hours, a 20% aqueous KOH solution was added dropwise at 0° C. The reaction mixture was filtered through Celite (trade name) and the filtrate was washed with a 1N KOH solution. The organic layer was concentrated by distilling off the solvent under reduced pressure. The residue was purified by chromatography on a silica gel column (hexane/ethyl acetate=4/1 to 3/1), followed by recrystallization from hexane-ethyl acetate, whereby 6.1 g (yield: 75%) of 3-methyl-2-naphthylamine was obtained.

$^1H$ NMR(CDCl$_3$, 300 MHz) 2.36(s,3H), 3.79(br,2H), 7.01(s,1H), 7.22(t,J=7.5 Hz,1H), 7.33(t,J=7.5 Hz,1H), 7.55 (s,1H), 7.59(d,J=8.1 Hz,1H), 7.65 (d,J=8.1 Hz,1H). $^{13}C$ NMR(CDCl$_3$,75 MHz) 17.9, 108.6, 122.4, 125.3, 125.4, 127.0, 128.2, 128.7, 133.7, 143.4, 161.0.

2) Synthesis of 3,3'-dimethyl-1,1'-binaphthyl-2,2'-diamine

At 50° C., 3.1 g (20 mmol) of 3-methyl-2-naphthylamline, 6.5 g (40 mmol) of FeCl$_3$ and 80 mL of H$_2$O were stirred for 2 hours. To the reaction mixture was added 2 mL of concentrated hydrochloric acid at room temperature. The mixture was stirred at room temperature for 10 minutes. To the reaction mixture were added 20 mL of methylene chloride and 20 mL of a saturated aqueous ammonia solution. After vigorous stirring at room temperature, the reaction mixture was filtered over Celite and the filtrate was washed with methylene chloride. The organic layer was concentrated by distilling off the solvent under reduced pressure. The residue was purified by Florisil (trade name) and then by chromatography on a silica gel column (hexane/ ethyl acetate=4/1 to 3/1). By recrystallization from hexane-chloroform, 0.76 g (yield: 24%) of 3,3'-dimethyl-1,1'-binaphthyl-2,2'-diamine was obtained.

$^1H$ NMR (CDCl$_3$, 300 MHz) 2.45(s,6H), 3.45(br,4H), 7.01(d,J=8.1 Hz,2H), 7.15(t,J=7.5 Hz,2H), 7.22(t,J=7.5 Hz,2H), 7.70(s,2H), 7.75(d,J=8.1 Hz,2H) $^{13}C$ NMR (CDCl$_3$, 75 MHz) 18.4, 112.8, 122.4, 123.8, 125.2, 125.8, 127.3, 128.4, 128.9, 132.5, 142.1

3) Optical resolution of 3,3'-dimethyl-1,1'-binaphthyl-2,2'-diamine

Under an argon gas, 0.73 g (2.3 mmol) of 3,3'-dimethyl-1,1'-binaphthyl-2,2'-diamine and 1.6 g (1.7 mmol) of $RuCl_2$[(S)-binap](dmf)$_n$ were dissolved in methylene chloride. After stirring at room temperature for 2 hours, the solvent was distilled off under reduced pressure. The residue was purified by chromatography on a neutral silica gel column (methylene chloride), whereby 0.36 g (yield: 49%) of (R)-3,3'-dimethyl-1,1'-binaphthyl-2,2'-diamine and 1.2 g (yield: 47%) of an (S)-BINAP-Ru/(S)-diamine complex were obtained. The (R)-3,3'-dimethyl-1,1'-binaphthyl-2,2'-diamine was recrystallized in methylene chloride, diethyl ether and hexane, whereby 99%ee of the title compound was obtained. HPLC analysis of (R)-3HPLC (CHIRALCEL OD-H column, hexane/2-propanol=80:20, flow rate 0.7 mL/min, detection UV=254 nm) $t_R$ of R-isomer 12.7 min, $t_R$ of S-isomer 20.3 min.

$[\alpha]_D^{25}$=+101.5 (c=0.50, $CHCl_3$) $^1$H NMR of (S)-BINAP-Ru/(S)-diamine complex $^1$H NMR (300 MHz, $CDCl_3$) δ1.84 (s,6H), 3.95(d,J=9.6 Hz,2H), 4.70(d,J=8.7 Hz,2H), 6.25(d,J=8.7 Hz,2H), 6.48(d,J=4.2 Hz,8H), 6.67(t,J=7.2 Hz,2H), 6.77(d,J=8.4 Hz,2H), 7.02–7.20(m,8H), 7.29–7.39(m,8H), 7.48–7.55(m,4H), 7.69(d,J=16.8 Hz,2H), 7.74(d,J=8.1 Hz,2H), 8.01(br,4H), 8.18(m,2H).

Example 2

Asymmetric Inactivation and Asymmetric Activation of Racemic DM-BINAP-Ru Complex (Synthesis of $RuCl_2$[(S)-dm-binap][(S,S) -dpen]

Under an argon gas stream, 25 mg (0.05 mmol) of $[RuCl_2(C_6H_6)]_2$, 77 mg (0.11 mmol) of racemic DM-BINAP and 1.8 mL of DMF were charged in a Schlenk tube, followed by stirring at 100° C. for 10 minutes. The solvent was then distilled off at 50° C. under reduced pressure, whereby 102 mg (yield: 97%) of $RuCl_2$[(±)-dm-binap](dmf)$_n$ was obtained. To the resulting complex were added 16.4 mg (0.053 mmol) of (R)-3,3'-dimethyl-1,1'-binaphthyl-2,2'-diamine and 1.8 mL of methylene chloride were added. After stirring for 1 hour, the reaction mixture was cooled to 0° C. and 10 mg (0.05 mmol) of (S,S)-1,2-diphenylethylendiamine was added. After stirring at room temperature for 10 minutes, the solvent was distilled off under reduced pressure, whereby a mixture of $RuCl_2$[(S)-dm-binap][(S,S)-dpen] and $RuCl_2$[(R)-dm-binap][(R)-3,3'-dimethyl-1,1'-binaphthyl-2,2'-diamine] was obtained as a yellow solid (128 mg).

Example 3

Asymmetric Hydrogenation Reaction of 1'-acetonaphthone

A 100 mL autoclave was charged with 11.7 mg (0.010 mmol) of the mixture of $RuCl_2$[(S)-dm-binap][(S,S)-dpen] and $RuCl_2$[(R)-dm-binap][(R)-3,3'-dimethyl-1,1'-binaphthyl-2,2'-diamine] obtained in Example 2. After purging with argon, 2.8 mL of 2-propanol and 50 μL (0.025 mmol) of KOH/2-propanol (0.5M solution) were added. The resulting mixture was stirred at room temperature for 30 minutes. After addition of 0.38 mL (2.5 mmol) of 1'-acetonaphthone, stirring was conducted at room temperature for 4 hours at a hydrogen pressure adjusted to 0.8 Mpa. The reaction mixture was concentrated by distilling off the solvent under reduced pressure. The residue was filtered using silica gel, whereby 420 mg (yield: 98.7%) of (R)-1-(1-naphthyl)ethanol was obtained. The enantio-selectivity was 96.2%ee.

$[\alpha]_D^{25}$=+75.5 (c=1.0, $CHCl_3$) GC (column, CP-Cyclodextrin-β-2,3,6-M-19, i.d. 0.25 mm×25 m, CHROMPACK; carrier gas, nitrogen (75 kPa); column temp, 160° C.; injection temp, 190° C.; split ratio, 100:1), $t_R$ of S-isomer 31.6 min, $t_R$ of R-isomer 32.7 min.

Example 4

Synthesis of (R)-1-phenylethanol

Under similar conditions to those of Example 3 except for the use of acetophenone instead of 1'-acetonaphthone as a raw material, asymmetric hydrogenation was conducted. The conversion ratio was 100%, while the enantio-selectivity was 94.8%ee.

GC (column, CP-Cyclodextrin-β-2,3,6-M-19, i.d. 0.25 mm×25 m, CHROMPACK; carrier gas, nitrogen (75 kPa); column temp, 105° C.; injection temp, 135° C.; split ratio, 100:1), $t_R$ of R-isomer 17.5 min (97.4%), $t_R$ of S-isomer 19.2 min (2.6%).

Example 5

Synthesis of (R)-1-(2-tolyl)ethanol

Under similar conditions to those of Example 3 except for the use of 2-acetyltoluene instead of 1'-acetonaphthone as a raw material, asymmetric hydrogenation was conducted. The conversion ratio was 100%, while the enantio-selectivity was 95.4%ee.

GC (column, CP-Cyclodextrin-β-2,3,6-M-19, i.d. 0.25 mm×25 m, CHROMPACK; carrier gas, nitrogen (75 kPa); column temp, 130° C.; injection temp, 160° C.; split ratio, 100:1) $t_R$ of R-isomer 19.2 min (97.7%), $t_R$ of S-isomer 20.4 min (2.3%)

Example 6

Synthesis of (R)-1-(3-tolyl)ethanol

Under similar conditions to those of Example 3 except for the use of 3-acetyltoluene instead of 1'-acetonaphthone as a raw material, asymmetric hydrogenation was conducted. The conversion ratio was 100%, while the enantio-selectivity was 95.0%ee.

GC (column, CP-Cyclodextrin-β-2,3,6-M-19, i.d. 0.25 mm×25 m, CHROMPACK; carrier gas, nitrogen (75 kPa); column temp, 115° C.; injection temp, 145° C.; split ratio, 100:1), $t_R$ of R-isomer 19.2 min (97.5%), $t_R$ of S-isomer 20.4 min (2.5%)

Example 7

Synthesis of (R)-1-(4-tolyl)ethanol

Under similar conditions to those of Example 3 except for the use of 4-acetyltoluene instead of 1'-acetonaphthone as a raw material, asymmetric hydrogenation was conducted. The conversion ratio was 100%, while the enantio-selectivity was 93.0%ee.

HPLC (CHIRALCEL OB—H column, hexane/2-propanol=90:10, flow rate 0.5 mL/min, detection UV=254 nm) $t_R$ of S-isomer 12.4 min (3.5%), $t_R$ of R-isomer 14.6 min (96.5%).

Example 8

Synthesis of (R)-1-(2-naphthyl)ethanol

Under similar conditions to those of Example 3 except for the use of 2'-acetonaphthone instead of 1'-acetonaphthone as a raw material, asymmetric hydrogenation was conducted. The conversion ratio was 100%, while the enantio-selectivity was 90.6%ee.

HPLC (CHIRALPAK AS column, hexane/2-propanol= 98:2, flow rate 1.0 mL/min, detection UV=254 nm) $t_R$ of R-isomer 14.5 min (95.3%), $t_R$ of S-isomer 16.2 min (4.7%).

Comparative Example 1

Under an argon gas stream, 25 mg (0.05 mmol) of [RuCl$_2$(C$_6$H$_6$)]$_2$, 68 mg (0.11 mmol) of racemic BINAP and 1.8 mL of DMF were fed to a Schlenk tube, followed by stirring at 100° C. for 10 minutes. The solvent was then distilled off at 50° C. under reduced pressure, whereby RuCl$_2$[(±)-binap](dmf)$_n$ was obtained. To the resulting complex were added 15.1 mg (0.053 mmol) of (S)-1,1'-binaphthyl-2,2'-diamine and 1.8 mL of methylene chloride. After stirring for 1 hour, the solvent was distilled off under reduced pressure, whereby a yellow solid was obtained.

To 100 mL of an autoclave was charged 11.7 mg (0.010 mmol) of the mixture of RuCl$_2$[(R)-binap](dmf)$_n$ and RuCl$_2$[(S) -binap][(S)-binaphthyldiamine]. After purging with argon, 2.8 mL of 2-propanol and 50 μL (0.025 mmol) of KOH/2-propanol (0.5M solution) were added. The resulting mixture was stirred at room temperature for 30 minutes. After addition of 0.38 mL (2.5 mmol) of 1'-acetonaphthone, stirring was conducted at room temperature for 4 hours at a hydrogen pressure adjusted to 0.8 Mpa. The reaction mixture was concentrated by distilling off the solvent under reduced pressure. The residue was filtered using silica gel, whereby 228 mg (yield: 53%) of (R)-1-(1-naphthyl)ethanol was obtained. The enantio-selectivity was 4%ee.

Comparative Example 2

Under an argon gas stream, 25 mg (0.05 mmol) of [RuCl$_2$(C$_6$H$_6$)]$_2$, 68 mg (0.11 mmol) of (S)-BINAP and 1.8 mL of DMF were fed to a Schlenk tube, followed by stirring at 100° C. for 10 minutes. The solvent was then distilled off at 50° C. under reduced pressure, whereby RuCl$_2$[(S)-binap](dmf)$_n$ was obtained. To the resulting complex were added 15.1 mg (0.11 mmol) of (S)-1,1'-binaphthyl-2,2'-diamine and 1.8 mL of methylene chloride were added. After stirring for 1 hour, the solvent was distilled off under reduced pressure, whereby a yellow solid was obtained.

To 100 mL of an autoclave was fed 11.7 mg (0.010 mmol) of RuCl$_2$[(S)-binap][(S)-binaphthyldiamine]. After purging with argon, 2.8 mL of 2-propanol and 50 μL (0.025 mmol) of KOH/2-propanol (0.5M solution) were added. The resulting mixture was stirred at room temperature for 30 minutes. After addition of 0.38 mL (2.5 mmol) of 1'-acetonaphthone, stirring was conducted at room temperature for 4 hours at a hydrogen pressure adjusted to 0.8 Mpa. The reaction mixture was concentrated by distilling off the solvent under reduced pressure. The residue was filtered using silica gel, whereby 202 mg (yield: 47%) of (R)-1-(1-naphthyl)ethanol was obtained. The enantio-selectivity was 30%ee.

According to the invention, an optically active ruthenium-phosphine complex can be synthesized by reacting a racemic ruthenium phosphine complex with ½ equivalent of an optically active chiral inactivating agent and then with an optically active diamine derivative.

By using the above-described complex, various optically active alcohols are available by an industrially advantageous process at a high purity, high yield and low cost.

While the invention has been described in detail and with reference to specific embodiments thereof, it will be apparent to one skilled in the art that various changes and modifications can be made therein without departing from the spirit and scope thereof.

This application is based on Japanese patent applications No. 2000-070220 filed on Mar. 14, 2000, the entire contents of which incorporated herein by reference.

What is claimed is:

1. A process for producing an optically active ruthenium-phosphine complex represented by the following formula (1):

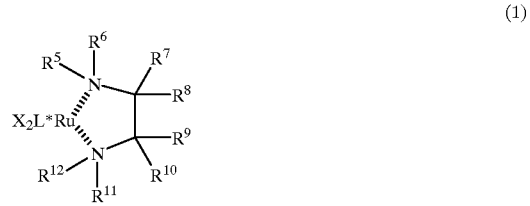

wherein $R^5$, $R^6$, $R^{11}$ and $R^{12}$ each independently represents a hydrogen atom, a saturated or unsaturated hydrocarbon group, an aryl group, a urethane group or a sulfonyl group;

$R^7$, $R^8$, $R^9$ and $R^{10}$ are the same or different so that the carbon to which these substituents have been bonded becomes an asymmetric center and each independently represents a hydrogen atom, an alkyl group, an aromatic monocyclic or polycyclic group, a saturated or unsaturated hydrocarbon group or a cyclic hydrocarbon group; or $R^7$ or $R^8$, and $R^9$ or $R^{10}$ may be coupled together to form an alicyclic group so that the carbon bonded thereto becomes an asymmetric center;

L represents a bidentate ligand compound of a tertiary phosphine;

X represents a halogen atom; and

* means chiral center (L* is an optically active substance), which comprises reacting a ruthenium-phosphine complex represented by the following formula (2):

wherein X and L have the same meanings as defined above (L is a racemic modification);

A represents triethylamine (Et$_3$N) or dimethylformamide (DMF); and m, n, p and q each stands for an integer and when A represents Et$_3$N, m, n, p and q stand for 2, 4, 2 and 1, respectively, and when A represents DMF, m, n, p and q stand for 1, 2, 1 and 2 to 5, respectively;

or a ruthenium-phosphine complex represented by the following formula (3):

wherein,

X and L have the same meanings as defined above (L is a racemic modification), and D represents benzene, p-cymene, 1,3,5-trimethylbenzene or hexamethylbenzene, with ½ equivalent of an optically active chiral diamine represented by the following formula (4):

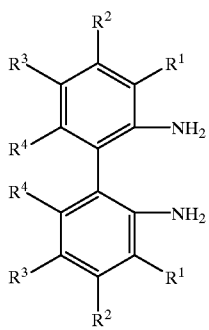

(4)

wherein,
R¹ represents a $C_{1-4}$ lower alkyl group, R² represents a hydrogen atom, a methyl group or a methoxy group, R³ represents a hydrogen atom, a methyl group, a methoxy group or a chlorine atom, R⁴ represents a methyl group, a methoxy group or a trifluoromethyl group, or R³ and R⁴ may be coupled together to form a cyclo ring, thereby inactivating only one of the enantiomers, and then reacting the resulting compound with an optically active diamine derivative represented by the following formula (5):

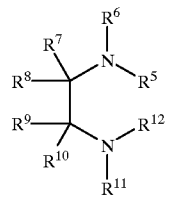

(5)

wherein,
R⁵, R⁶, R⁷, R⁸, R⁹, R¹⁰, R¹¹ and R¹² have the same meanings as defined above,
thereby activating the other enantiomer.

* * * * *